(12) United States Patent
Gustafson et al.

(10) Patent No.: US 7,537,732 B2
(45) Date of Patent: May 26, 2009

(54) METHOD AND APPARATUS FOR ASSAYING WOOD PULP FIBERS

(75) Inventors: Richard Gustafson, Bellevue, WA (US);
James B. Callis, Seattle, WA (US);
Jeffrey D. Mathews, Neenah, WI (US);
John Robinson, Issaquah, WA (US);
Carsten A. Bruckner, San Mateo, CA (US); Kuntinee Suvamakich, Seattle, WA (US)

(73) Assignee: University of Washington, Seattle, WA (US)

( * ) Notice: Subject to any disclaimer, the term of this patent is extended or adjusted under 35 U.S.C. 154(b) by 925 days.

(21) Appl. No.: 10/788,548

(22) Filed: Feb. 26, 2004

(65) Prior Publication Data

US 2005/0019948 A1 Jan. 27, 2005

Related U.S. Application Data

(60) Provisional application No. 60/450,306, filed on Feb. 27, 2003.

(51) Int. Cl.
*G01N 33/487* (2006.01)
(52) U.S. Cl. .............. 422/82.05; 422/82.06; 422/82.08; 422/50; 356/318
(58) Field of Classification Search ................. 436/164, 436/172; 422/82.05, 82.06, 82.08
See application file for complete search history.

(56) References Cited

U.S. PATENT DOCUMENTS 3,065,148 A * 11/1962 Ferrari ......................... 435/40
4,172,524 A * 10/1979 Holm et al. ................... 209/524
4,837,446 A * 6/1989 Renard et al. ............. 250/461.1
5,113,454 A 5/1992 Marcantonio et al. ........ 382/108
5,216,483 A 6/1993 Berthold et al. .............. 356/318
5,330,621 A 7/1994 Visuri et al. ................... 162/49
5,428,441 A * 6/1995 Ogino et al. ................... 356/73
5,436,717 A 7/1995 Ogino ........................... 356/72
5,486,915 A * 1/1996 Jeffers et al. ................. 356/318
5,582,982 A * 12/1996 Cubbage et al. ................. 435/6
5,902,749 A * 5/1999 Lichtwardt et al. ............. 436/50
6,806,955 B2 * 10/2004 Jang ............................ 356/318

OTHER PUBLICATIONS

Patsayeva, S., V. Yuzhakov, M. Lamotte, R. Fantoni, A. Lai, and A. Palucci. "Variation of the UV-To-Blue Fluorescence Ratio for Organic Matter in Water Under Conditions of Fluorescence Saturation" Proceedings of EARSeL-SIG-Workshop LIDAR, Dresden/FRG, Jun. 16-17, 2000. pp. 157-164.

* cited by examiner

*Primary Examiner*—Jill Warden
*Assistant Examiner*—Cedric Chan
(74) *Attorney, Agent, or Firm*—Ronald M. Anderson (57) ABSTRACT

Paper pulp is added to a stain solution. The stain solution and pulp fibers are mixed to form a slurry. Samples are removed from the slurry and are admixed with dilution water and a bleach. Then, the fibers are moved into a flow cell where they are subjected to a light source adapted to stimulate fluorescence from the stained pulp fiber. Before the fiber slurry enters the flow cell it is mixed with a dilution water of bleach to reduce background fluorescence. The fluorescent light is collimated and directed through a dichroic filter onto a fluorescence splitting dichroic filter.

19 Claims, 4 Drawing Sheets

METHOD AND APPARATUS FOR ASSAYING WOOD PULP FIBERS

RELATED APPLICATION

A claim of priority is made based on our provisional application Ser. No. 60/450,306, filed Feb. 27, 2003, and entitled Method and Instrument to Measure Single Fibers Properties by Application of Fluorescent Stains. This provisional application is hereby incorporated herein by this specific reference.

GOVERNMENT RIGHTS

This invention was funded with government support under Contract Number DE-FC07-97-ID13539 awarded by the U.S. Department of Energy, and the U.S. government may have certain rights in this invention.

TECHNICAL FIELD

This invention relates to the provision of a method and apparatus for using fluorescent stained wood pulp fibers and a light beam to analyze and measure properties of interest in the wood pulp fibers. More particularly, it relates to the provision of a method and apparatus for determining chemical properties of the wood pulp fibers, for measuring geometric properties such as fiber length and shape, and for assessing the uniformity of wood pulp used in the manufacture of paper.

BACKGROUND OF THE INVENTION

Wood fibers are the building blocks of paper and pulp products. Typically, properties of fibers, especially chemical properties, are measured on a macroscopic pulp sample that contains millions of fibers. While this information is essential to run unit operations in the mill, it is not sufficient to produce a final product with optimal properties. To truly optimize the performance in the pulp and paper mill requires that critical properties be measured on the single fiber level. With single fiber measurements, the uniformity (as well as the average values) of critical variables may be optimized and controlled. The result will be a globally optimized product that will have superior performance over that product which is controlled only by using averages of critical properties.

Instruments are available on the market today that can measure the geometric properties of single pulp fibers. These instruments can measure fiber length, coarseness, and fiber shape. In addition, some claim to be able to measure cell wall thickness. Mills routinely use these analyzer to assess and optimize the fiber's geometric properties to make the grade of paper currently being produced on their paper machine. Mills typically have fiber geometry specifications that include both average fiber properties as well as something about the uniformity of that fiber property.

An object of the present invention is to provide an apparatus and method that can measure fiber geometry characteristics, both the averages and the distributions, and critical chemical properties of the single fibers, such as lignin content (kappa number) or fiber charge. There is no instrument presently available that can measure this full suite of important fiber properties. It is also an object of the present invention to provide an apparatus and method by which paper makers will be able to correlate single fiber properties, such as comparing the relation between Kappa number and fiber shape, and, most importantly, develop relationships that allow them to determine the original profile of fiber properties and produce desirable grades of paper on their paper machine.

BRIEF SUMMARY OF THE INVENTION

The present invention includes preparing a pulp fiber sample to be analyzed. The preparation method comprises preparing a fluorescent stain solution, adding a predetermined amount of pulp fibers to a predetermined amount of the stain solution; and mixing the pulp fibers and the stain solution to disperse the pulp fibers in the stain solution and create a slurry. Then, a pulp fiber solution is removed from the slurry and mixed with a second solution to form a pulp fiber suspension. Preferably, the second solution is a bleach. Preferably also, dilution water and bleach are present in an amount sufficient to permit reaction of the bleach with the stain in solution to an extent desired without an undesirable amount of reaction of the bleach with stain that is bound to the pulp fiber.

Another aspect of the invention is the provision of a method of analyzing a pulp fiber sample. In preferred form, a flow cell is provided. The flow cell includes a passageway having an inlet, an outlet, and a region between the inlet and the outlet that has a transparent wall. A pulp fiber sample that includes a pulp fiber and a fluorescent stain bound to the pulp fiber is directed into the inlet of the flow cell, and from said inlet into the region between the inlet and outlet that includes the transparent wall. While the pulp fiber sample is in this region, a light source is used to direct light through the transparent wall into the pulp fiber sample to stimulate fluorescence from the pulp fiber sample while it is in the flow cell. Then, fluorescence from the pulp sample is analyzed to measure at least one property of interest in the pulp fiber sample.

A further aspect of the invention is to provide an apparatus for analyzing pulp fiber. Such apparatus comprises a flow cell that includes a passageway having an inlet, an outlet and a sample holding region between the inlet and the outlet that has a transparent wall. A conduit delivers a pulp fiber sample to the inlet of the flow cell. The pulp fiber sample flows through the inlet into the sample holding region of the flow cell. The pulp fiber sample includes pulp fiber and a fluorescent stain bound to the pulp fiber. A light beam projector is provided that includes a light source and a lens for producing a beam of light from the light source. The beam of light is directed to one side of a first dichroic mirror that extends approximately forty-five degrees with respect to the beam of light. The pulp fiber sample holding region of the flow cell is spaced from the dichroic mirror. An objective lens is positioned between the sample holding region of the flow cell and the first dichroic mirror and creates a substantially straight image path that extends at about a forty-five degree angle with respect to the first dichroic mirror and substantially perpendicular to the light beam. A second dichroic mirror is positioned on the side of the first dichroic mirror that is opposite the light source, the focusing lens, the flow cell and the objective lens. The second dichroic mirror extends at an angle that is substantially perpendicular to the first dichroic mirror. In use, the image beam passes through the first dichroic mirror to the second dichroic mirror. A first wavelength portion of the image beam also passes through the second dichroic mirror. Another wavelength portion is reflected by the second dichroic mirror. A first camera is provided for recording the image that passes through the second dichroic mirror and a second camera is provided for recording the image that is reflected by the second dichroic mirror. Data obtained by the cameras is directed to a computer and in the computer is processes for determining properties of the pulp fiber sample.

Other objects, advantages and features of the invention will become apparent from the description of the best mode set forth below, from the drawings, from the claims and from the principles that are embodied in the specific structures and steps that are illustrated and described.

BRIEF DESCRIPTION OF THE SEVERAL VIEWS OF THE DRAWING

Like reference numerals used to designate like parts throughout the several views of the drawing, and.

DETAILED DESCRIPTION OF THE INVENTION

Figure 1:
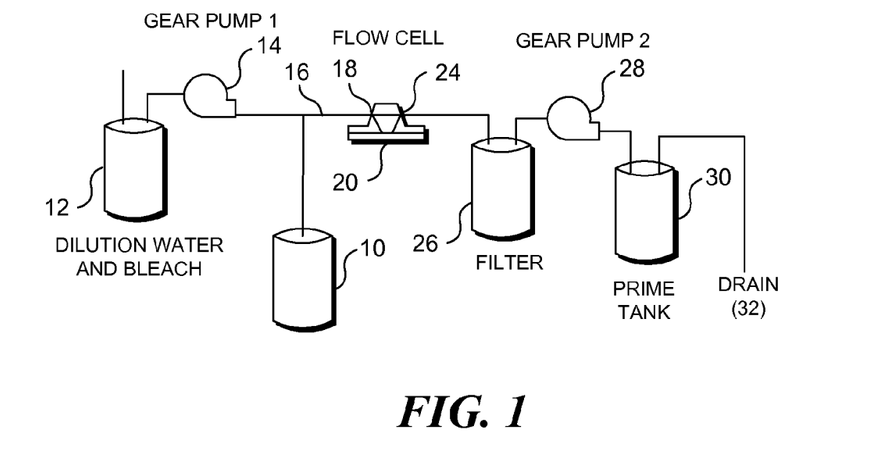
FIG. 1 is a flow diagram of apparatus for preparing fiber samples for analysis, showing a flow cell in which a fiber suspension is imaged.
Figure 2:
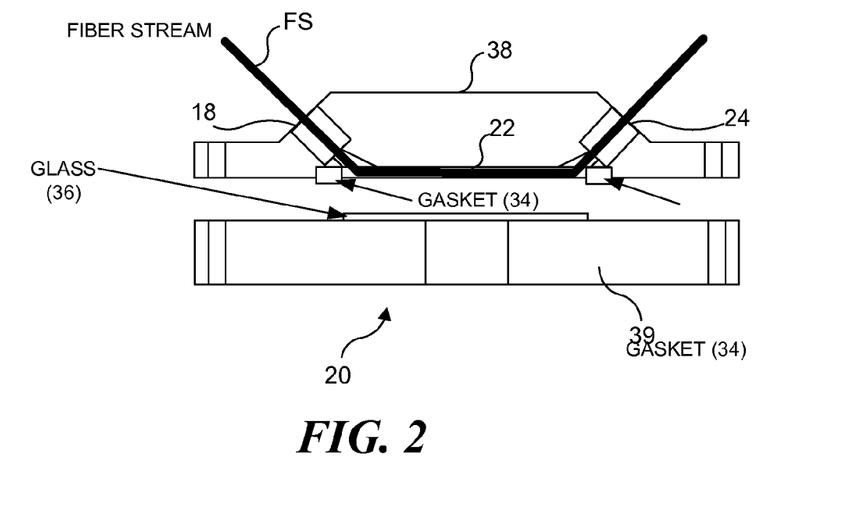
FIG. 2 is an enlarged scale view of the flow cell shown in FIG. 1.
Figure 3:
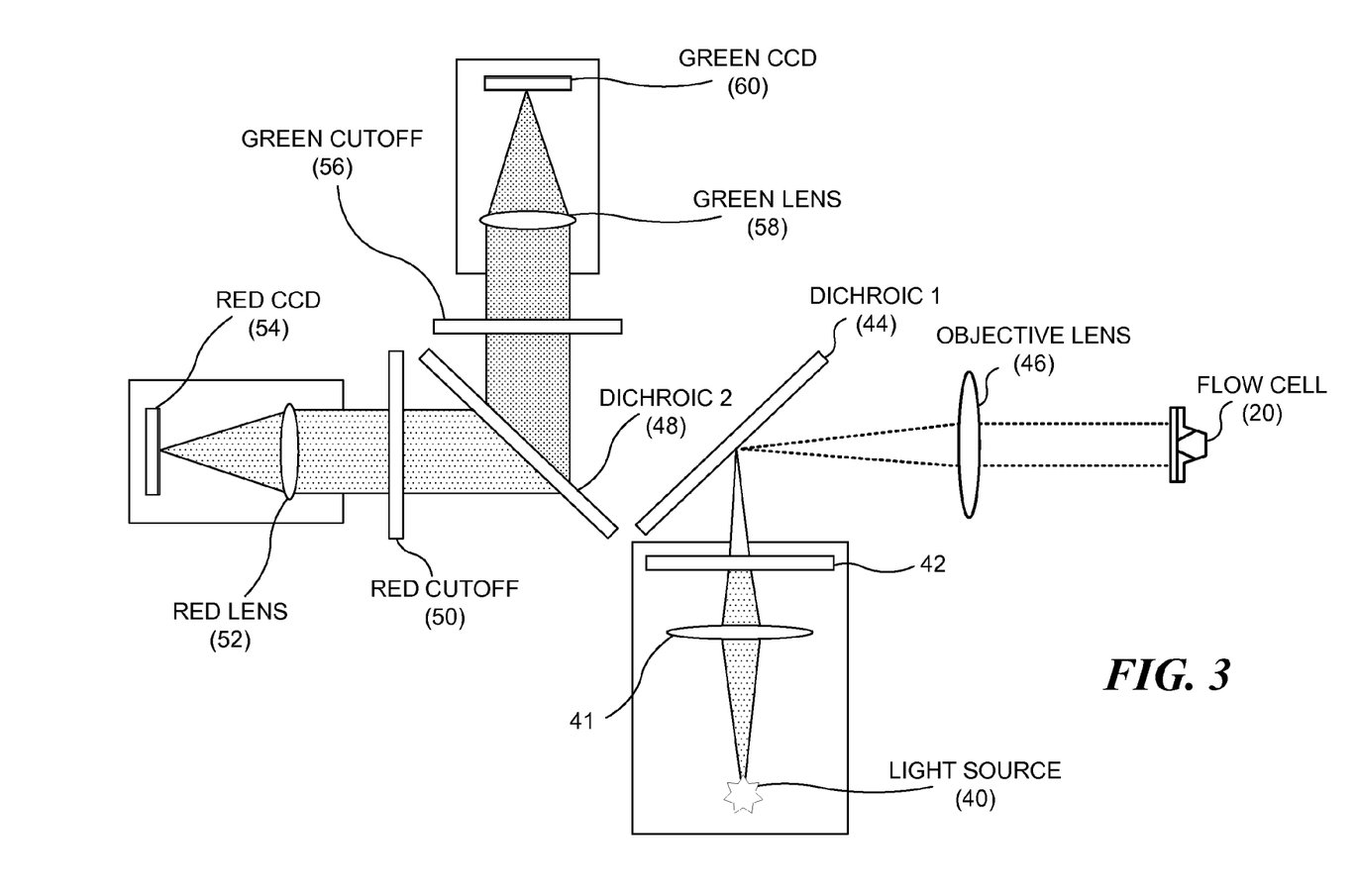
FIG. 3 is a diagram of an optical system which is used to analyze fiber samples while they are in the flow cell.
Figure 4:
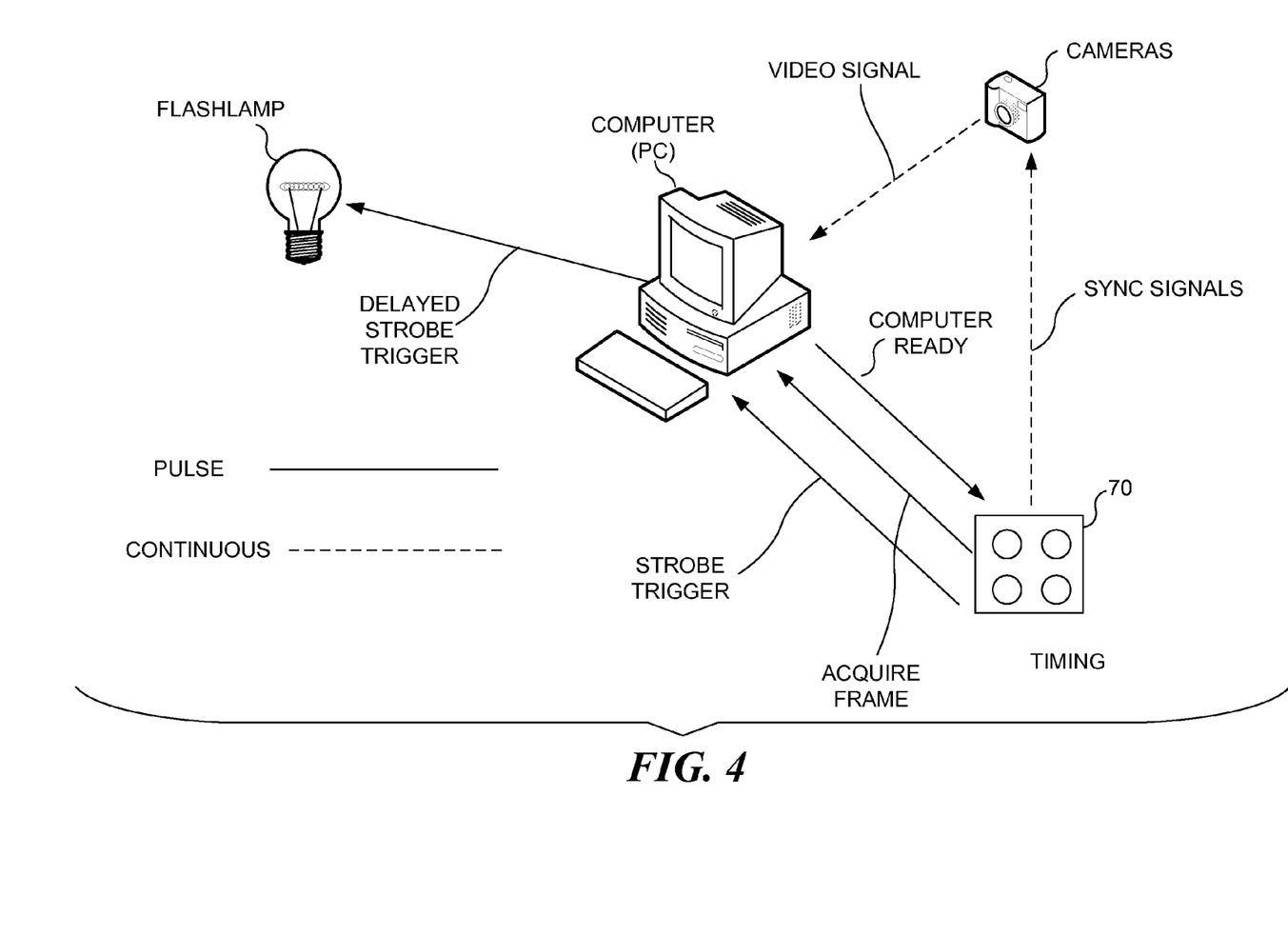
FIG. 4 is a connectivity diagram illustrating how the hardware components of the system communicate with each other, including solid lines representing pulses and dashed lines representing continuous signals.

The fiber analyzer of the present invention includes a sample handling fluid system, shown by FIGS. 1 and 2; an optical system shown by FIG. 3, and a data analyzing system shown by FIG. 4. The sample handling fluid system includes a flow cell having a sensing zone in which wood fiber samples can be illuminated as images, and pumps and conduits for causing a sample carrying liquid to flow into, through, and out from the sensing zone. The optical system includes a light source for illuminating the fiber samples while they are in the sensing zone of the flow cell, and apparatus for recording fluorescent images of the fibers. The data analyzing system operates to convert the recorded images into useful data.

Referring to FIG. 1, a container 10 includes stained wood pulp fibers. A container 12 contains dilution water and bleach. A suitable pump 14 (e.g. a gear pump) removes the solution of dilution water and bleach from container 12 and delivers it through a conduit 16 that leads to the inlet 18 of a flow cell 20. The relative flow rates of fibers and bleach are controlled to achieve a specific background fluorescence. Pump 14 pulls stained fibers out from the container 10 and admixes them with the solution from container 12 in the conduit 16. The suction created from pump 14 may, by way of example, be about 30 ml/min. The dilution water and bleach solution is removed from container 12 at this rate and mixes with the fiber sample in the conduit 16 upstream of the inlet 18 leading into the flow cell 20. In the preferred embodiment, the solution from container 10 mixes with the stained fiber sample in a tee union positioned approximately two inches in front of the inlet 18 leading into the flow cell 20. After mixing, the sample/solution mixture enters into the flow cell 20 and for a while is in an imaging zone 22 that is between the inlet 18 and an outlet 24. The effluent from the flow cell 20 is directed into a filter 26 in which the fibers are filtered from the liquid, such as by use of a 5 µm cartridge filter, and the liquid is pumped out of the system by use of a second pump 28 (e.g. a gear pump). The outlet of the pump 28 leads into a prime tank 30 (e.g. a 500 ml tank). Tank 30 functions to ensure that the pump 28 will not lose its prime when the system is shut off. The liquid exiting the tank 30 flows to a drain 32. By way of example, the tubing in the system shown by FIG. 1 may be ¼ inch OD polyethylene tubing and the fittings may be ¼ inch polypropylene fittings.

An enlarged scale view of the flow cell 20 is shown by FIG. 2. Flow cell 20 includes a gasket 34 that is sandwiched between a piece of plexiglass 38 and a window cut from a microscope slide 36. The fiber sampling containing solution enters and exits through the inlet 18 and the outlet 24 that are formed in the member 38 of the flow cell 20. A channel is formed in the member 38. This channel may measure about 500 µm deep, about 3 cm long and about 1 cm wide. The inlet 18 leads into one end of the channel and the outlet 24 leads out from the opposite end of the channel. The inlet opening 18 and outlet opening 24 are threaded for receiving a fitting (not shown) used to connect tubing to the member 38. In FIG. 2, the fiber stream is designated FS. In FIG. 2, the fiber stream FS is shown in space. In reality, a first tubing (not shown) is connected to the inlet 18 by a first fitting (not shown). A second tubing (not shown) is connected to the outlet opening 24 by another fitting (not shown). The channel is formed in a plexiglass member that is attached to member 38. The glass member 36 extends over and covers the open side of the channel when the members 38, 36 are together. The gasket 34 is an annular member and it surrounds the channel and seals its ends so that there is no leakage.

A negligible amount of fluorescence is observed from the plexiglass on the back of the flow cell 20. It is desirable to keep the flow cell fluorescence at a low level. Background fluorescence from the stain in solution can present problems if care is not taken. In order to obtain good measurements of fluorescent particles in the sample, the solution fluorescence must be reduced to a permissible level. A first way of doing this is to keep the gasket thickness as thin as possible without creating plugging problems in the channel. Secondly, according to an aspect of the invention, a small amount of bleach is added to the dilution water that is mixed with the stained fiber stream upstream of the analysis zone 22 in the flow cell 20. The bleach is added an amount sufficient so that the stain in solution reacts with the bleach must faster than the reaction of the bleach with the stain bound to the fiber. That is, the bleach is present in the dilution water in an amount sufficient to permit reaction of the bleach with the stain in solution to an extent desired without an undesirable amount of reaction of the bleach with stain that is bound to the pulp fiber sample.

An additional precaution can be taken to control the reaction of fiber bound stain with bleach. Rather than bleaching all of the background fluorescence with an uncontrolled excess of bleach, the background fluorescence is kept at a low level with feedback control of the pump 22. The bleach concentration in solution is quickly reduced by this control before much bound stain can react with the bleach. A simple proportional/integral controller will provide the amount of control performance that is desired.

The optical system resembles a modern fluorescence microscope. Epi-illumination is used to minimize excitation light pollution in the fluorescence images. An extended path length is used to fit all of the necessary filters between the objective and imaging lenses.

Referring to FIG. 3, the apparatus that is illustrated includes a suitable light source 40, e.g. a xenon strobe lamp, which outputs light from the ultraviolet to infrared wavelengths. This light passes through a blue light filter 42 which removes any light outside of the desired range for excitation. A dichroic mirror 44 is positioned to reflect the excitation light to an objective lens 46 that focuses the light onto the fibers in the flow cell 20. A "dichroic" mirror reflects some wavelengths of light and transmit the remaining wavelengths of light. The excitation light stimulates fluorescence from the stained fibers in the flow cell 20. The fluorescent light is then collimated by the objective lens 46. All of this light then passes back through the excitation dichroic filter 44 onto a fluorescence splitting dichroic filter 48. One target wavelength (e.g. red) passes through a cutoff filter 50 and then to the imaging lens 52 where it is focused through the cameras IR filter onto a CCD 54. Light of a different wavelength (i.e. green light) is reflected by the fluorescence splitting dichroic member 48 to and through a bandpass filter 56 and then onto an imaging lens 58 which focuses the light on a green CCD.

By way of example, a kappa measurement will be described in which the sample is stained by use of an Acridine Orange stain. The blue pass filter 42 removes any light outside of the 420 nm to 490 nm band. A dichroic mirror 44, centered at 500 nm, is used to reflect the blue light onto the objective lens 46 where it is focused onto the fibers in the flow cell 20. The blue excitation light stimulates fluorescence from the Acridine Orange in the flow cell. The fluorescent light, which has wavelengths between 500 nm and 730 nm (green to red range), is collimated by the objective lens 46. The green and red light then pass back through the excitation dichroic filter 44 onto the fluorescence splitting dichroic filter 48 centered at 580 nm. Red light passes to the red cutoff filter (long pass at 590 nm), and then to the imaging lens 50 where it is focused through the cameras infrared filter (low pass at 680 nm) onto the red channel CCD 54. The green fluorescence, which was reflected at the fluorescence spinning dichroic member 48, passes through a green pass filter (510 nm to 570 nm), and is then focused by an imaging lens 58 onto a green channel CCD 60.

Optical magnification in the illustrated system is about 0.64×. This is set by the ratio of the imaging lens focal length to the objective lens focal length. The objective lens is a 55 mm focal length lens designed for a 35 mm camera. The imaging lenses are two identical video lenses with 35 mm focal lengths. At this magnification, a CCD pixel is 13 μm×13 μm, and the entire 400 by 400 pixel image covers 0.5 cm×0.5 cm. This size is large enough that most fibers are not cut off by the edge of the image.

Light collection efficiency must be maximized in this system in order to get a reasonable signal to noise ratio in the CCD cameras. It was necessary to use two inch filters to keep the collimated light path as wide as possible. The result of the large diameter lenses and filters is that the system has a small depth of focus of about 500 μm, and loss of intensity at the image edges to about 60 percent of the maximum (vignetting). The depth of focus is not a significant problem because the flow cell 20 must be narrow in order to minimize the background fluorescence. Image vignetting is corrected before the images are processed.

Two simultaneous images, one from each camera, timed with a flash, must be captured and then processed to extract a particle fluorescence ratio. Typically, two wavelengths are required. One wavelength is specific for the property being measured and the other wavelength is a reference stain that corrects the image intensity with respect to general variables that can effect fluorescence intensity such as cell wall thickness. Mostly off-the-shelf components along with some custom built hardware accomplish this task. A PC fitted with frame grabbers and a data acquisition card controls the entire process. A LabView program controls the computer task involved in timing and image acquisition.

Figure 5:
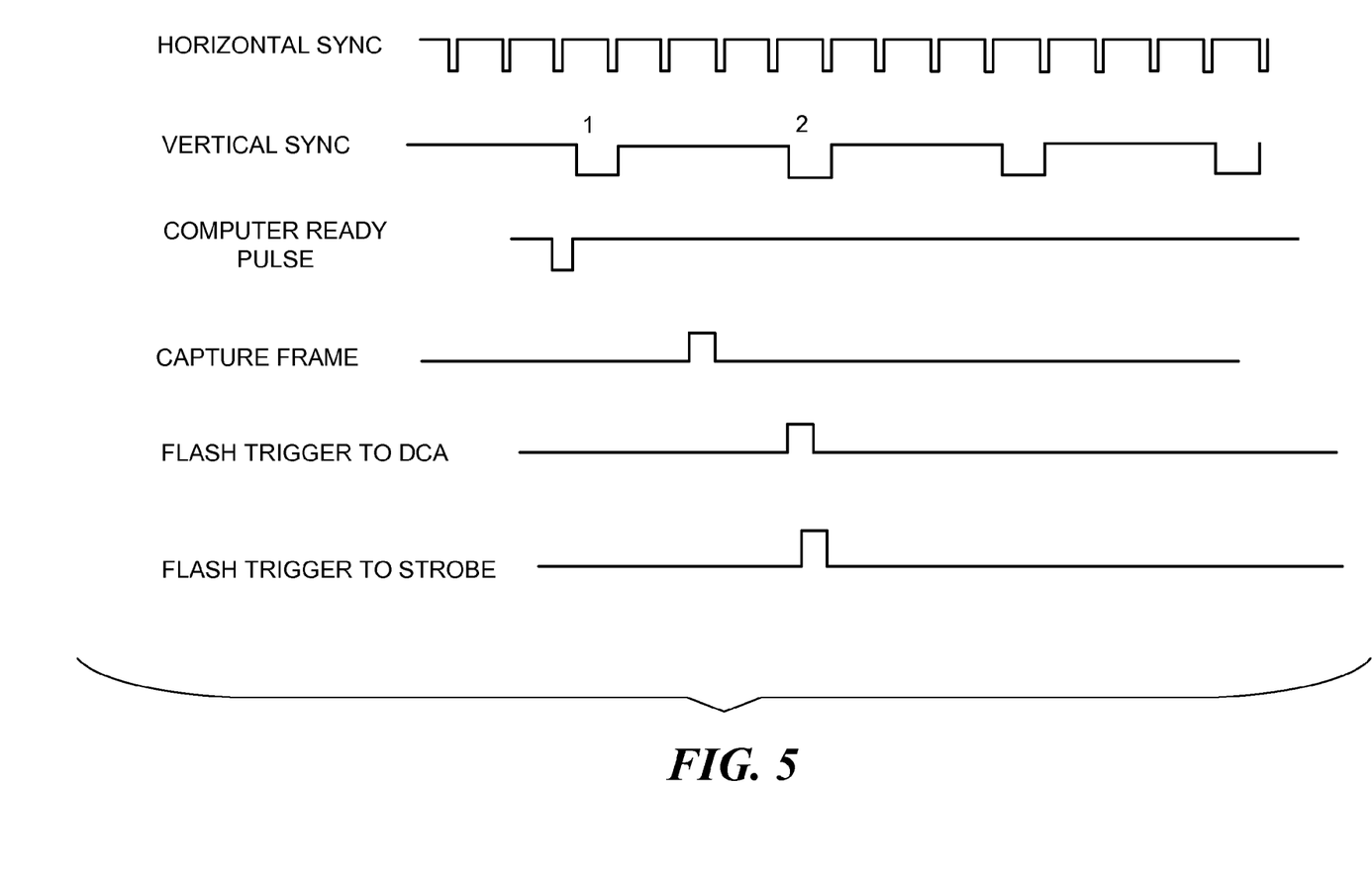
FIG. 5 is a diagram illustrating an order of timing events.

FIG. 5 is a conductivity diagram showing how all of the hardware components communicate. The solid lines in FIG. 5 represent pulses. The dashed lines represent continuous signals.

Video synchronization is the first step to making the instrument work. An external sync generator provides the same type sync signal to the two cameras. The sync generator has horizontal sync outputs providing negative pulses at 15.625 kHz with a pulse width of 4.7 μsec. The vertical sync outputs are negative pulses at 25 Hz with a width of 450 μsec. Using these sync signals, the two cameras operate together, including shuttering at the same time.

The instrument operates semi-synchronously. The flash 62 occurs only when the computer PC is ready to collect another frame, and only that frame is transferred into computer memory, but all the action is timed from the vertical sync signal. The flash 62 requires additional timing, because the flash 62 must be triggered during the correct frame, and during the 1/4000th of a second that the shutter allows the camera 64 to integrate. FIG. 5 illustrates the order of timing events. The computer PC sends a pulse to the sync generator/timing box 70 (FIG. 4) when it is ready to capture an image. The timing box 70 waits for the first vertical sync and then sends a 20 msec delayed high pulse to the triggers of the two frame grabbers (halfway between the first and second vertical sync pulses). On the second vertical sync pulse, the timing box sends a strobe trigger to the computer's data acquisition card (DAC). The (DAC) adds a 1750 μsec delay to the trigger and then passes it to the flashlamp trigger input. The delay is necessary to cause the flash to occur during the 1/4000th sec window that the camera shutters are allowing the CCD's to integrate light. After the integrated frames from the two color channels are transferred to analog video signals, the awaiting frame grabbers in the PC digitize the signals and pass the information into the computer memory where it can be accessed within the LabView environment.

Once the images are present in computer memory, processing begins to take place. The first step in image processing is correction. The dark-current image is subtracted from the raw image. Then the raw images from each color channel are multiplied by the vignette correction images that flatten the fields and calibrate the color sensitivity of the two cameras. A quick binary threshold is performed, and the number of bright pixels in the image is counted by summing the binary image intensity. If there are too few bright pixels to make up a fiber, the image is dumped and the computer goes back into acquisition mode.

If there are particles in the images, the corrected images are passed for further analysis. Background estimation is performed using a low pass filter. This separates the fluorescent stained fibers from the solution and flow cell fluorescence. The background is subtracted from the corrected image leaving fibers and noise, and then a threshold is applied to locate the fibers. Then a subroutine quantifies the mean red and green intensities, perimeter, and area of the objects. The final processing step is classifying the particle shapes. A subprogram performs an algorithm that yields kink and curl indices of the fibers. A special filter is then applied to each object, identifying endpoints in the object. Any object with more than two ends is flagged as a fiber clump. The data for each fiber are catalogued into an array of fiber records, and the program loops back to acquisition mode. After the user stops acquisition, fiber data are saved as an array in a spreadsheet file.

The following is an overview of the staining and analysis protocols. Analysis involves preparing the stained fiber sample, and running the instrument.

1) Make up a stock stain solution.
2) Add about 0.1 g OD of pulp to 1 liter of the stain solution, and disburse the fibers by mixing in a blender.
3) Place the slurry in a one-liter beaker and allow it to stir for ten minutes with a magnetic stirrer. After ten minutes, the sample is ready for analysis.

The instrument described above can be used to make the basic chemical and morphological measurements on pulp fibers. The wavelengths used in the analyses depend on the stains being used and may be easily modified to get the best signal to noise ratio with whatever dye has been selected. The instrument can also be easily modified to measure signal intensity at more than two wavelengths if such measurements were needed. For example, if you were measuring multiple chemical properties on fibers simultaneously.

The following is a list of the components that are shown in FIG. 3:

| | | | |
|---|---|---|---|
| Red CCD | 54 | #XC8500CE/BW Camera Module | Sony 550 Madison Avenue New York, NY 10022 888-476-6972 |
| Red Lens | 52 | #HF35A-2M1/BW Camera Module Lens | Sony |
| Red Cutoff Filter | 50 | #03 FCG 098/Red Filter #03 FCG 101/Red Filter | Melles Griot 55 Science Parkway Rochester, NY 14620 585-241-2279 |
| Dichroic 2 | 48 | #585 DCXR/Dichroic #2 | Chroma Tech. 74 Cotton Mill Hill Brattleboro, VT 05301 1-800-824-7662 |
| Green Cutoff Filter | 56 | #D252 50 m/Green Filter | Chroma Tech. |
| Green Lens | 58 | #HF35A-2M1/BW Camera Module Lens | Sony |
| Green CCD | 60 | #XC8500CE/BW Camera Module | Sony |
| Dichroic 1 | 44 | #490 DCLP/Dichroic #1 | Chroma Tech. |
| Blue Filter | 42 | #D455 70 m/Blue Filter | Chroma Tech. |
| Converging Lens | 41 | #H32-982/2 in Dia 6 in FL Lens | Edmund Industrial Optics 101 East Glouchester Pike Barrington, NJ 08007-1380 800-363-1992 |
| Arc Lamp | 40 | OSRAM 5000K Arc Lamp | OSRAM SYLVANIA 100 Endicott Street Danvers, MA 01923 978-777-1900 |
| Objective Lens | 46 | Carl Zeiss/Planar 1,4/50 | Carl Zeiss Carl Zeiss Str. 4-54 73447 Oberkochen Germany (0049) 7364-20 6175 |

The instrument can also be easily modified to handle larger on smaller particles. This would increase the applicability of the instrument in the paper mill and make it useful for industries such as pharmaceuticals and food processing. To image smaller or larger particles would require minor modifications to the flow cell and the instrument optics.

The illustrated embodiment is only one example of the present invention and, therefore, is non-limitive. It is to be understood that many changes in the particular structure, materials, and features of the invention may be made without departing from the spirit and scope of the invention. Therefore, it is our intention that our patent rights not be limited by the particular embodiment that is illustrated and described herein, but rather be determined by the following claims, interpreted according to accepted doctrines of claim interpretation, including use of the doctrine of equivalents.

What is claimed is:

1. Apparatus for analyzing pulp fiber, comprising:
   a flow cell that includes a passageway having an inlet, an outlet and a sample holding region between the inlet and the outlet that has a transparent wall;
   a conduit for delivering a pulp fiber sample to the inlet of the flow cell, and through the inlet into the sample holding region of the flow cell, said pulp fiber sample including pulp fiber and a fluorescent stain bound to the pulp fiber;
   a light source and a focused light path positioned to direct light through the transparent wall into the pulp fiber sample to stimulate fluorescence from the pulp fiber sample while it is in the flow cell;
   means for reducing an amount of stain in solution in the flow cell to an extent desired without undesirably reducing an amount of stain that is bound to the pulp fiber sample; and
   a fluorescence analyzer to analyze fluorescence emitting from the pulp fiber sample and measure at least one property of the sample.

2. The apparatus of claim 1, wherein the light source is a xenon strobe lamp which outputs light from ultraviolet to infrared wavelengths, and said apparatus includes a filter that removes light outside of a desired range, a mirror used to reflect light from the filter towards the transparent wall of the flow cell, and an objective lens disposed between the mirror and the transparent wall for focusing the light on the pulp fiber sample in the flow cell, the mirror being configured to both reflect light from the filter towards the pulp fiber sample in the flow cell and to enable fluorescence from the pulp fiber sample in the flow cell to pass through the mirror before reaching a detector logically coupled to the fluorescence analyzer.

3. The apparatus of claim 1, further comprising:
   a first dichroic mirror configured to direct light from the light source to the pulp fiber sample in the flow cell;
   a second dichroic mirror configured to direct light from the pulp fiber sample in the flow cell, the second dichroic mirror allowing light having a first wavelength to pass through the second dichroic mirror, while reflecting light having a second wavelength, such that no additional optical element is disposed between the first and second dichroic mirrors;
   a first detector configured to receive the light at the first wavelength that has passed through the second dichroic mirror and produce a corresponding first output signal; and
   a second detector configured to receive the light at the second wavelength that has been reflected by the second dichroic mirror and produce a second output signal.

4. The apparatus of claim 1, wherein the apparatus is configured such that light from the light source used to stimulate fluorescence from the pulp fiber sample and fluorescence emitted from the pulp fiber sample pass through the same transparent wall of the flow cell.

5. The apparatus of claim 1, wherein the fluorescence analyzer is configured to determine a fiber geometry, a total charge of the fiber, and a lignin content of the pulp fiber sample.

6. The apparatus of claim 1, wherein the fluorescence analyzer comprises:
   a first camera configured to capture light having a first wavelength to produce a first image;
   a second camera configured to capture light having a second wavelength to produce a second image;
   synchronization means for ensuring synchronous acquisition of the first and second images by the first camera and the second camera; and
   the fluorescence analyzer being configured to process the first and second images by implementing the following functions:
      multiplying the first and second images by a vignette correction image that flattens a field and calibrates a color sensitivity of each of the first and second cameras to achieve a calibrated image;

applying a binary threshold to the calibrated image to determine a number of bright pixels in the calibrated image; and determining if the number of bright pixels indicates that the calibrated image includes a fiber, such that images not including a fiber are discarded, while images including a fiber are further processed.

7. The apparatus of claim 6, wherein the fluorescence analyzer is configured to further process images including a fiber by implementing the following functions:

subtracting a dark-current image from the first and second images to generate a corrected image;

performing a background estimation using a low pass filter;

subtracting the background estimation from the corrected image to achieve a filtered image including fibers and noise;

applying a threshold to locate the fibers in the filtered image; and quantifying mean intensities for the first and second wavelengths, perimeters of the fibers that were located, and an area of the fibers.

8. The apparatus of claim 7, wherein the fluorescence analyzer is configured to further process images including a fiber by calculating kink and curl indices of the fibers that were located.

9. The apparatus of claim 7, wherein the fluorescence analyzer is configured to further process images including a fiber by identifying endpoints for each fiber located, and discarding data corresponding to any fiber located that includes more than two endpoints.

10. A system for analyzing pulp fiber, comprising:

a flow cell that includes a passageway having an inlet, an outlet, and a sample holding region between the inlet and the outlet that has a transparent wall;

a conduit for delivering a pulp fiber sample to the inlet of the flow cell, and through the inlet into the sample holding region of the flow cell, said pulp fiber sample including pulp fiber and a fluorescent stain bound to the pulp fiber;

a light source and a focused light path to direct light through the transparent wall into the pulp fiber sample to stimulate fluorescence from the pulp fiber sample while it is in the flow cell; and means for analyzing fluorescence emitted from the pulp fiber sample to determine at least one property of the pulp fiber sample, said means processing first and second images of the pulp fiber sample by implementing the following functions:

multiplying the first and second images by a vignette correction image that flattens a field and calibrates a color sensitivity of each of the first and second cameras to achieve a calibrated image;

applying a binary threshold to the calibrated image to determine a number of bright pixels in the calibrated image; and determining whether the number of bright pixels indicates that the calibrated image includes a fiber, such that images not including a fiber are discarded, while images including a fiber are further processed.

11. Apparatus for analyzing pulp fiber, comprising:

a flow cell that includes a passageway having an inlet, an outlet, and a sample holding region between the inlet and the outlet that has a transparent wall;

a conduit for delivering a pulp fiber sample to the inlet of the flow cell, and through the inlet into the sample holding region of the flow cell, said pulp fiber sample including pulp fiber and a fluorescent stain bound to the pulp fiber;

a light source and a focused light path positioned to direct light through the transparent wall into the pulp fiber sample to stimulate fluorescence from the pulp fiber sample while it is in the flow cell; and means to analyze fluorescence emitted from the pulp fiber sample to determine a fiber geometry, a total charge of the fiber, and a lignin content of the pulp fiber sample.

12. Apparatus for analyzing pulp fiber, comprising:

a flow cell that includes a passageway having an inlet, an outlet and a sample holding region between the inlet and the outlet that has a transparent wall;

a conduit for delivering a pulp fiber sample to the inlet of the flow cell, and through the inlet into the sample holding region of the flow cell, said pulp fiber sample including pulp fiber and a fluorescent stain bound to the pulp fiber;

a light source and a focused light path positioned to direct light through the transparent wall into the pulp fiber sample to stimulate fluorescence from the pulp fiber sample while it is in the flow cell;

a first detector configured to receive fluorescence from the pulp fiber sample in the flow cell;

a first dichroic mirror configured to both direct light from the light source to the pulp fiber sample in the flow cell and to enable fluorescence from the pulp fiber sample in the flow cell to pass through the first dichroic mirror before reaching the first detector, the first dichroic mirror being spaced apart from the transparent wall along a substantially straight image path that is substantially perpendicular to a beam of light emitted by the light source; the first dichroic mirror being disposed between the flow cell and the first detector; and a fluorescence analyzer positioned to analyze fluorescence emitting from the pulp fiber sample and measure at least one property of the sample.

13. Apparatus for analyzing pulp fiber, comprising:

a sample chamber for receiving a pulp fiber sample, the pulp fiber sample having been stained with a reagent that when stimulated will fluoresce and emit stimulated light having a predefined waveband including a plurality of different wavelengths;

a light source configured to emit light capable of stimulating the reagent to fluoresce;

a dichroic mirror configured to split the stimulated light into a first portion and a second portion;

a first detector configured to receive the first portion of stimulated light;

a second detector configured to receive the second portion of stimulated light; and a fluorescence analyzer configured to analyze data from the first and second detectors corresponding to fluorescence emitted from the stained pulp fiber sample and measure at least one property of the pulp fiber sample, wherein the fluorescence analyzer is configured to utilize data provided by the first detector to apply a correction to data provided by the second detector.

14. Apparatus for analyzing pulp fiber, comprising:

a sample chamber for receiving a pulp fiber sample, the pulp fiber sample having been stained with a reagent that when stimulated will fluoresce and emit stimulated light having a predefined waveband including a plurality of different wavelengths;

a light source configured to emit light capable of stimulating the reagent to fluoresce;

a dichroic mirror configured to split the stimulated light into a first portion and a second portion;

a first detector configured to receive the first portion of stimulated light;

a second detector configured to receive the second portion of stimulated light; and a fluorescence analyzer configured to analyze data from the first and second detectors corresponding to fluorescence emitted from the stained pulp fiber sample and measure at least one property of the pulp fiber sample, wherein the fluorescence analyzer is configured to extract a particle fluorescence ratio from data provided by the first and second detectors.

15. The apparatus of claim 13, wherein the fluorescence analyzer is configured to utilize corrected data provided by the second detector to measure the at least one property of the pulp fiber sample.

16. Apparatus for analyzing pulp fiber, comprising:
a sample chamber for receiving a pulp fiber sample, the pulp fiber sample having been stained with a reagent that when stimulated will fluoresce and emit stimulated light having a predefined waveband including a plurality of different wavelengths;
a light source configured to emit light capable of stimulating the reagent to fluoresce;
a dichroic mirror configured to split the stimulated light into a first portion and a second portion;
a first detector configured to receive the first portion of stimulated light;
a second detector configured to receive the second portion of stimulated light; and
a fluorescence analyzer configured to analyze data from the first and second detectors corresponding to fluorescence emitted from the stained pulp fiber sample and measure at least one property of the pulp fiber sample, wherein the dichroic mirror is centered at about 580 nanometers, the first detector is configured to acquire data for light ranging from about 510 nm to about 570 nm, and the second detector is configured to acquire data for light ranging from about 590 nm to about 680 nm.

17. Apparatus for analyzing pulp fiber, comprising:
a sample chamber for receiving a pulp fiber sample, the pulp fiber sample having been stained with a reagent that when stimulated will fluoresce and emit stimulated light having a predefined waveband including a plurality of different wavelengths;
a light source configured to emit light capable of stimulating the reagent to fluoresce;
a dichroic mirror configured to split the stimulated light into a first portion and a second portion;
a first detector configured to receive the first portion of stimulated light;
a second detector configured to receive the second portion of stimulated light; and
a fluorescence analyzer configured to analyze data from the first and second detectors corresponding to fluorescence emitted from the stained pulp fiber sample and measure at least one property of the pulp fiber sample, wherein the second detector includes an infrared filter configured to allow light below about 680 nm to pass through the infrared filter, and further comprising a second filter disposed between the dichroic mirror and the second detector, the second filter being configured to allow light above about 590 nm to pass through the second filter, the infrared filter and the second filter in combination allowing light ranging from about 590 nm to about 680 nm to reach the second detector.

18. Apparatus for analyzing pulp fiber, comprising:
a flow cell that includes a passageway having an inlet, an outlet, and a sample holding region between the inlet and the outlet that has a transparent wall;
a conduit for delivering a pulp fiber sample to the inlet of the flow cell, and through the inlet into the sample holding region of the flow cell, said pulp fiber sample including pulp fiber and a fluorescent stain bound to the pulp fiber;
a light source and a focused light path positioned to direct light through the transparent wall into the pulp fiber sample to stimulate fluorescence from the pulp fiber sample while it is in the flow cell;
means for controlling an amount of stain in solution in the flow cell to an extent desired without undesirably reducing an amount of stain that is bound to the pulp fiber sample, said means comprising:
a bleach fluid volume including a volume of bleach solution;
a slurry fluid volume including a volume of pulp fiber slurry including a stain both in solution and bound to the pulp fibers, the slurry fluid volume being coupled in fluid communication with the conduit;
a bleach solution supply line coupled in fluid communication with the bleach fluid volume and the conduit; and
a pump configured to drive the bleach solution and the pulp fiber slurry into the conduit to provide the pulp fiber sample, the pump controlling a relative ratio of bleach solution to pulp fiber slurry, such that the amount of bleach solution present in the flow cell is sufficient to bleach substantially all of the stain in solution, generally without bleaching the stain bound to the pulp fiber sample; and
a fluorescence analyzer positioned to analyze fluorescence emitting from the pulp fiber sample and measure at least one property of the sample.

19. Apparatus for analyzing pulp fiber, comprising:
a flow cell that includes a passageway having an inlet, an outlet, and a sample holding region between the inlet and the outlet that has a transparent wall;
a conduit for delivering a pulp fiber sample to the inlet of the flow cell, and through the inlet into the sample holding region of the flow cell, said pulp fiber sample including pulp fiber and a fluorescent stain bound to the pulp fiber;
a light source and a focused light path positioned to direct light through the transparent wall into the pulp fiber sample to stimulate fluorescence from the pulp fiber sample while it is in the flow cell;
means to control an amount of stain in solution in the flow cell to an extent desired without undesirably reducing an amount of stain that is bound to the pulp fiber sample, said means comprising:
a fluid volume including a volume of bleach solution; and
a bleach solution supply line coupled in fluid communication with the fluid volume and the conduit, the bleach solution supply line being coupled in fluid communication with the conduit at a location proximate the inlet of the flow cell, such that before the pulp fiber sample passes through the flow cell, the bleach solution bleaches substantially all of the stain in solution, generally without bleaching the stain bound to the pulp fiber sample; and
a fluorescence analyzer positioned to analyze fluorescence emitting from the pulp fiber sample and measure at least one property of the sample.

* * * * *

UNITED STATES PATENT AND TRADEMARK OFFICE
CERTIFICATE OF CORRECTION

PATENT NO. : 7,537,732 B2  Page 1 of 1
APPLICATION NO. : 10/788548
DATED : May 26, 2009
INVENTOR(S) : Gustafson et al.

It is certified that error appears in the above-identified patent and that said Letters Patent is hereby corrected as shown below:

| | |
|---|---|
| Title Page, Item (75) Inventors: | "Kuntinee Suvamikich" should read --Kuntinee Suvarnakich-- |
| Column 1, line 15 | "This invention was funded with government support under Contract Number DE-FC07-97-ID13539 awarded by the U.S. Department of Energy, and the U.S. government may have certain rights in this invention." should read --This invention was made with U.S. Government support under Contract Number DE-FC07-97-ID13539 awarded by the U.S. Department of Energy. The U.S. Government has certain rights in the invention.-- |
| Column 1, line 51 | "analyzer" should read --analyzers-- |
| Column 4, line 35 | after "added" insert --in-- |
| Column 7, line 45 | "on" should read --or-- |
| Column 9, line 40 (Claim 10, line 10) | after "path" insert --positioned-- |

Signed and Sealed this

First Day of September, 2009

David J. Kappos
*Director of the United States Patent and Trademark Office*